US011491150B2

(12) United States Patent
Li et al.

(10) Patent No.: US 11,491,150 B2
(45) Date of Patent: Nov. 8, 2022

(54) ORGANIC COMPOUNDS

(71) Applicant: INTRA-CELLULAR THERAPIES, INC., New York, NY (US)

(72) Inventors: Peng Li, New Milford, NJ (US); Youyi Peng, Plainsboro, NJ (US); Lawrence P. Wennogle, Hillsborough, NJ (US); Qiang Zhang, Plainsboro, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 7 days.

(21) Appl. No.: 15/986,485

(22) Filed: May 22, 2018

(65) Prior Publication Data

US 2018/0333403 A1 Nov. 22, 2018

Related U.S. Application Data

(60) Provisional application No. 62/509,597, filed on May 22, 2017.

(51) Int. Cl.
*A61K 31/454* (2006.01)
*A61P 13/12* (2006.01)
*A61P 3/10* (2006.01)

(52) U.S. Cl.
CPC .............. *A61K 31/454* (2013.01); *A61P 3/10* (2018.01); *A61P 13/12* (2018.01)

(58) Field of Classification Search
CPC ........... A61K 31/454; A61P 3/10; A61P 13/12
See application file for complete search history.

(56) References Cited

U.S. PATENT DOCUMENTS

| 7,799,782 B2 | 9/2010 | Munson et al. |
| 8,143,272 B2 | 3/2012 | Mazurov et al. |
| 9,108,949 B2 | 8/2015 | Peng et al. |
| 9,469,625 B2 | 10/2016 | Li et al. |
| 2004/0147522 A1 | 7/2004 | Wong et al. |
| 2004/0220170 A1 | 11/2004 | Atkinson et al. |
| 2006/0019984 A1 | 1/2006 | Groppi et al. |
| 2009/0092578 A1* | 4/2009 | Su .................. C07K 16/1203 424/85.2 |
| 2010/0179186 A1 | 7/2010 | Papke et al. |
| 2015/0174128 A1* | 6/2015 | Tester .................. A61K 31/506 514/235.2 |
| 2018/0235988 A1* | 8/2018 | Huizing ............. A61K 31/7008 |

FOREIGN PATENT DOCUMENTS

| EP | 2723173 B1 * | 4/2017 | ............. A61K 31/41 |
| WO | WO 2003/037274 | 5/2003 | |
| WO | WO 2004/099154 | 11/2004 | |
| WO | WO 2005/000821 | 1/2005 | |
| WO | WO-2006116808 A1 * | 11/2006 | ............. A61K 38/17 |
| WO | WO 2009/112459 | 9/2009 | |
| WO | WO 2012/178112 | 12/2012 | |

OTHER PUBLICATIONS

Arneric, et al., "Neuronal nicotinic receptors: A perspective on two decades of drug discovery research," Biochem. Pharmacol., 74: 1092-1101 (2007).
Atkinson, R., et al., "Preparation of pyrazole-amides and sulfonamides as sodium channel moderators," CAS: 141: 395577 (2004).
Buckingham, S., et al., "Nicotinic Acetylcholine Receptor Signalling: Roles in Alzheimer's Disease and Amyloid Neuroprotection," Pharmacological Reviews, 61(1): 39-61 (2009).
Chang, C.C., "Looking Back on the Discovery of α-Bungarotoxin," J. Biomed. Sci., 6: 368-375 (1999).
Cucina, A., et al., "Nicotine-induced smooth muscle cell proliferation is mediated through BFGF and TGF-β1," Surgery, 127(3): 316-322 (2000).
Cucina, A., et al., "Nicotine induces platelet-derived growth factor release and cytoskeletal alteration in aortic smooth muscle cells," Surgery, 127(1): 72-78 (2000).
Cucina, A., et al., "Nicotine Regulates Basic Fibroblastic Growth Factor and Transforming Growth Factor β1 Production in Endothelial Cells," Biochemical and Biophysical Research Communications, 257(2): 306-312 (1999).
Davies, A., et al., "Characterisation of the binding of [3H]methyllycaconitine: a new radioligand for labelling α7-type neuronal nicotinic acetylcholine receptors," Neuropharmacology, 38: 679-690 (1999).
Flores, C.M., et al., "A subtype of nicotinic cholinergic receptor in rat brain is composed of alpha 4 and beta 2 subunits and is up-regulated by chronic nicotine treatment," Mol. Pharmacol., 41(1): 31-37 (1992).
Heeschen, C., et al., "A novel angiogenic pathway mediated by non-neuronal nicotinic acetylcholine receptors," J. Clin. Invest., 110: 527-536 (2002).
Henchman, R., et al., "Ligand-Induced Conformational Change in the α7 Nicotinic Receptor Ligand Binding Domain," Biophysical Journal, 88(4): 2564-2576 (2005).
Hua, P., et al., "Nicotine worsens the severity of nephropathy in diabetic mice: implications for the progression of kidney disease in smokers," Am. J. Physiol. Renal Physiol., 299: F732-F739 (2010).
International Search Report for International Application No. PCT/US2012/043880, dated Oct. 23, 2012, 3 pages.
Jensen, A., et al., "Neuronal Nicotinic Acetylcholine Receptors: Structural Revelations, Target Identifications, and Therapeutic Inspirations," J. Med. Chem., 48(15): 4705-4745 (2005).
Jones, I., et al., "α7 Nicotinic Acetylcholine Receptor Expression in Alzheimer's Disease," Journal of Molecular Neuroscience, 30(1-2): 83-84 (2006).
Lindstrom, J., et al., "Structure and function of neuronal nicotinic acetylcholine receptors," Progress in Brain Research, 109: 125-137 (1996).

(Continued)

*Primary Examiner* — Jeffrey S Lundgren
*Assistant Examiner* — Ibrahim D Bori
(74) *Attorney, Agent, or Firm* — Hoxie & Associates LLC

(57) ABSTRACT

The disclosure relates to compounds and methods of treatment relating to nicotinic receptor antagonists. For example, the compounds and methods of treatment function block the activity of certain acetylcholine receptors and subtypes therein, and are useful treating diseases and conditions mediated by nicotinic receptor stimulation, e.g., diabetes mellitus, chronic kidney disease, acute kidney failure, and reduction of blood glucose levels.

14 Claims, No Drawings

(56) References Cited

OTHER PUBLICATIONS

Lukas et al., "International Union of Pharmacology. XX. Current Status of the Nomenclature for Nicotinic Acetylcholine Receptors and Their Subunits," Pharmacol. Rev., 51(2): 397-401 (1999).
Mazurov, A., et al., "Selective α7 Nicotinic Acetylcholine Receptor Ligands," Current Medicinal Chemistry, 13: 1567-1584 (2006).
Nishioka, T., et al., "Sensitization of epithelial growth factor receptors by nicotine exposure to promote breast cancer cell growth," Breast Cancer Research, 13(6): R113, 1-11 (2011).
Obert, D., et al., "Environmental Tobacco Smoke Furthers Progression of Diabetic Nephropathy," Am. J. Med. Sci., 341(2): 126-130 (2011).
Olincy, A., et al., "Proof-of-Concept Trial of an α7 Nicotinic Agonist in Schizophrenia," Arch. Gen. Psychiatry, 63: 630-638 (2006).
Paleari, L., et al., "Inhibition of non-neuronal α7-nicotinic receptor reduces tumorigenicity in A549 NSCLC xenografts," Int. J. Cancer, 125: 199-211 (2009).
Papke, R., et al., "Activation and Desensitization of Nicotinic α7-type Acetylcholine Receptors by Benzylidene Anabaseines and Nicotine," The Journal of Pharmacology and Experimental Therapeutics, 329(2): 791-807 (2009).
Peng, Y., et al., "Discovery of novel α7 nicotinic receptor antagonists," Bioorganic & Medicinal Chemistry Letters, 20: 4825-4830 (2010).
Registry [STN online], entered Oct. 26, 2007, RN: 951602-39-4.
Registry [STN online], entered Mar. 13, 2008, RN: 1007754-83-7.
Registry [STN online], entered Jun. 1, 2008, RN: 1024146-34-6.
Registry [STN online], entered Sep. 26, 2008, RN: 1053148-42-7.
Registry [STN online], entered Nov. 2, 2008, RN: 1069822-46-3.
Registry [STN online], entered Apr. 15, 2009, RN: 1135071-68-9.
Registry [STN online], entered Jul. 30, 2009, RN: 1170376-73-4.
Registry [STN online], entered Feb. 22, 2010, RN: 1207020-03-8.
Registry [STN online], entered Feb. 22, 2010, RN: 1207057-14-4.
Registry [STN online], entered Mar. 25, 2010, RN: 1214456-33-3.
Registry [STN online], entered Sep. 17, 2010, RN: 1241973-12-5.
Registry [STN online], entered Jan. 28, 2011, RN: 1260998-72-8.
Registry [STN online], entered Apr. 10, 2011, RN: 1277529-93-7.
Registry [STN online], entered Apr. 10, 2011, RN: 1277736-60-3.
Registry [STN online], entered Apr. 10, 2011, RN: 1277737-34-4.
Registry [STN online], entered Apr. 10, 2011, RN: 1277798-76-1.
Registry [STN online], entered Apr. 12, 2011, RN: 1279078-00-0.
Registry [STN online], entered Apr. 13, 2011, RN: 1279270-42-6.
Registry [STN online], entered Apr. 29, 2011, RN: 1287554-44-2.
Registry [STN online], entered May 2, 2011, RN: 1288944-52-4.
Registry [STN online], entered May 3, 2011, RN: 1289322-69-5.
Registry [STN online], entered May 5, 2011, RN: 1290321-69-5.
Registry [STN online], entered May 5, 2011, RN: 1290321-74-2.
Registry [STN online], entered May 5, 2011, RN: 1290550-37-6.
Registry [STN online], entered May 18, 2011, RN: 1296508-55-8.
Registry [STN online], entered May 24, 2011, RN: 1299716-67-8.
Registry [STN online], entered May 29, 2011, RN: 1302490-94-3.
Rezonzew, G., et al., "Nicotine exposure and the progression of chronic kidney disease: role of the α7-nicotinic acetylcholine receptor," Am. J. Physiol. Renal Physiol., 303: F304-F312 (2012).
Ritz, E., et al., "Effects of Smoking on Renal Hemodynamics in Healthy Volunteers and in Patients with Glomerular Disease," J. Am. Soc. Nephrol., 9: 1798-1804 (1998).
Rodriguez-Loaiza, P., et al., "Click Chemistry on Solid Phase: Parallel Synthesis of N-Benzyltriazole Carboxamides as Super-Potent G-Protein Coupled Receptor Ligands," Journal of Combinatorial Chemistry, 8: 252-261 (2006).
Roncarati, R., et al., "Procognitive and Neuroprotective Activity of a Novel α7 Nicotinic Acetylcholine Receptor Agonist for Treatment of Neurodegenerative and Cognitive Disorders," J. Pharmacol. Exp. Ther., 329(2): 459-468 (2009).
Sacco, K., et al., "Nicotinic receptor mechanisms and cognition in normal states and neuropsychiatric disorders," J. Psychopharmacol., 18(4): 457-474 (2004).
Sciamanna, M., et al., "Nicotinic Acetylcholine Receptors of Muscle and Neuronal (α7) Types Coexpressed in a Small Cell Lung Carcinoma," J. Neurochem., 69: 2302-2311 (1997).
Singh, S., et al., "Nicotinic Acetylcholine Receptor Signaling in Tumor Growth and Metastasis," Journal of Oncology, 2011: 1-11 (2011).
Spindel, E.R., "Is Nicotine the Estrogen of Lung Cancer?" American Journal of Respiratory and Critical Care Medicine, 179: 1081 (2009).

* cited by examiner

ORGANIC COMPOUNDS

CROSS REFERENCE TO RELATED APPLICATIONS

This application claims priority to and the benefit of U.S. Provisional Application No. 62/509,597, filed on May 22, 2017, the contents of which are incorporated herein by reference.

TECHNICAL FIELD

The field generally relates to organic compounds that act as nicotinic acetylcholine alpha-7 receptor antagonists. The field further relates to the use of nicotinic receptor modulators, i.e., antagonists, for use as a prophylaxis and/or treatment for diabetes mellitus, chronic kidney disease consequent to diabetic neuropathy, acute kidney failure, nicotine-exacerbated chronic kidney disease, chronic kidney disease in the absence of nicotine exacerbation, and reduction of blood glucose levels.

BACKGROUND OF THE DISCLOSURE

Nicotinic acetylcholine receptors (nAChRs) belong to the Cys-loop subfamily of pentameric ligand-gated ion channels and can be classified into muscle-type and neuronal subtypes. The neuronal nAChRs comprise twelve subunits ($\alpha$2-$\alpha$10 and $\beta$2-$\beta$4) with different arrangements, while the muscle-type is consisted of four subunits in a single arrangement of $\alpha$1$\gamma\alpha$1$\beta\delta$ (c is replaced by e in the adult). (Lukas, R. J. et al., *Pharmacol. Rev.* 1999, 51, 397) Two major neuronal receptors a4b2 and $\alpha$7 have been identified in the central nervous system. (Flores, C. et al., *Mol. Pharmacol.* 1992, 41, 31; Lindstrom J. et al., *Prog. Brain Res.* 1996, 109, 125) The neuronal $\alpha$7 nAChR has been proposed as a potential therapeutic target for a broad range of neurodegenerative and psychiatric diseases, including Alzheimer's disease, schizophrenia, anxiety, and epilepsy.

A variety of selective partial and full agonists have been developed for the $\alpha$7 nAChR as potential therapeutics. (Jensen A. et al., *Prog., Brain Res.* 1996) Several $\alpha$7 nAChR selective agonists (e.g., TC-5619 and MEM-3454) have advanced to clinical trials for Alzheimer's disease and schizophrenia. (Arneric, S. P. et al., *Biochem. Pharmacol.* 2007, 74, 1092; Mazurov A. et al., *Curr. Med. Chem.* 2006, 13, 1567; Olincy A., *Arch. Gen. Psychiatry* 2006, 63, 630) Although extensive efforts have been taken to identify selective $\alpha$7 nAChR agonists, the development of $\alpha$7 selective antagonists is relatively limited. Some studies have reported that certain naturally derived compounds may be incorporated as $\alpha$7 selective antagonists. For example, the krait *Bungarus multicinctus* derived peptide toxin a-bungarotoxin ($\alpha$-BTX) and the seeds of Delphinum isolated nonpetide toxin methyllycaconitine (MLA) are two frequently used $\alpha$7 selective antagonists. (Chang, C. C. et al. *J. Biomed. Sci.* 1999, 6, 368; Davies, A. R., et al. *Neuropharmacology* 1999, 38, 679)

Unfortunately, $\alpha$-BTX is a potent antagonist for muscle-type nAChRs as well, and both compounds also inhibit nAChR subtypes $\alpha$9 and $\alpha$9a10. (Jensen, A. A., et. al. *J. Med. Chem.* 2005, 48, 4705) Nevertheless, subtype-selective antagonists may possess intrinsic value as tools to define the roles played by $\alpha$7 nAChRs in the physiological and pathophysiological processes.

Indeed, and along these same lines, nicotinic acetylcholine receptors have been implicated as possible drug targets in a myriad of various disease states and for use as a possible measure for counter-terrorism purposes. In addition to uses in neurodegenerative and psychiatric diseases mentioned above, the $\alpha$7 nAChR has been implicated as having a role in nicotine-induced effects in chronic kidney disease. (Rezonzew G. et al., *Am J Physiol Renal Physiol* 303: F304-F312, 2012) Nicotine is responsible in part for the deleterious effects of tobacco smoking in the progression of chronic kidney disease and $\alpha$7 nAChR mediates these effects. Pharmacologic blockage of the $\alpha$7 nAchR reduces the deleterious effects of nicotine in the progression of chronic kidney disease.

Etiologies of chronic kidney disease differ widely, and include smoking tobacco, hypertension, diabetes mellitus, glomerulonephritis, interstitial nephritis, polycystic kidney disease, prolonged obstruction of the urinary tract, vesicoureteral, and other renal disorders. Diabetes was the primary cause of kidney failure in 2011, and was believed to represent 44% of all cases. It is estimated that as of 2015, 415 million people worldwide have a form of diabetes, with about 90% of cases being type 2 diabetes, with roughly equal incidence occurring in men and women. This represents a significant percentage of the worldwide adult population, and this number is expected to grow to about 642 million by the year 2040. While there is evidence that the $\alpha$7 nAChR plays a role in chronic kidney disease promoted by smoking tobacco, whether this receptor also plays a role in the progression of other models of chronic kidney disease, such as diabetic nephropathy, is not known.

For example, nicotine is known to have angiogenic effects in rodents that are inhibited by specific blockade of the $\alpha$7-nAChR, suggesting an important role of this nAChR receptor in these effects. (Heeschen, C. et al., A novel angiogenic pathway mediated by non-neuronal nicotinic acetylcholine receptors. *J Clin Invest* 2002, 110 (4), 527-36) In vascular endothelial and smooth muscle cells from bovine aorta, nicotine induces cell proliferation in a process mediated by increased generation of basic fibroblast growth factor (bFGF), platelet derived growth factor and TGF-$\beta$1. (see, e.g., Cucina, A. et al., Nicotine regulates basic fibroblastic growth factor and transforming growth factor beta1 production in endothelial cells. *Biochem Biophys Res Commun* 1999, 257 (2), 306-12; Cucina, A. et al., Nicotine-induced smooth muscle cell proliferation is mediated through bFGF and TGF-beta 1. *Surgery* 2000, 127 (3), 316-22; Cucina, A. et al., Nicotine induces platelet-derived growth factor release and cytoskeletal alteration in aortic smooth muscle cells. *Surgery* 2000, 127 (1), 72-8) In humans with IgA nephropathy, the administration of nicotine is associated with increased urinary albumin excretion and reductions in GFR as compared with healthy volunteers. (Ritz, E. et al., Effects of smoking on renal hemodynamics in healthy volunteers and in patients with glomerular disease. *J Am Soc Nephrol* 1998, 9 (10), 1798-804; Ritz, E. et al., Acute effects of cigarette smoking on renal hemodynamics. *Contrib Nephrol* 2000, 130, 31-8)

Previous studies have demonstrated that the administration of nicotine to rats with acute glomerulonephritis, diabetic mice or 5/6 nephrectomy model (5/6 Nx) rats, results in increased renal injury. (Rezonzew, G. et al., Nicotine exposure and the progression of chronic kidney disease: role of the alpha7-nicotinic acetylcholine receptor. *American journal of physiology. Renal physiology* 2012, 303 (2), F304-12) These studies showed that these effects are associated with increased NOX4 expression, increased TGF-$\beta$ production and increased ROS generation. (Hua, P. et al., Nicotine worsens the severity of nephropathy in diabetic mice: implications for the progression of kidney disease in smokers. *American journal of physiology. Renal physiology* 2010, 299 (4), F732-9) It has also been shown that in diabetic mice, the exposure to tobacco smoke results in increased mesangial expansion, along with increased fibronectin and TGF-β expression. (Obert, D. M. et al., Environmental tobacco smoke furthers progression of diabetic nephropathy. *The American journal of the medical sciences* 2011, 341 (2), 126-30) Rat kidneys have been shown to express the α7-nAChR and that pharmacologic blockade of the α7-nAChR with the non-selective cholinergic blocker methyllicaconitine (MLA) reduces the effects of nicotine on renal injury in a rat model of subtotal nephrectomy. (Rezonzew, G. et al., Nicotine exposure and the progression of chronic kidney disease: role of the alpha7-nicotinic acetylcholine receptor. *American journal of physiology. Renal physiology* 2012, 303 (2), F304-12)

However, despite the suggested links to chronic kidney disease, there are attendant issues with nicotinic acetylcholine receptors. For example, nicotinic acetylcholine receptors represent a complex and diverse set of receptor subtypes. Additionally, prolonged use may lead to desensitization of the receptor. Papke, et al., *Journal of Pharmacology and Experimental Therapeutics*, May 2009 vol. 329 no. 2 791-807. These latter factors have made it difficult to work with nicotinic acetylcholine receptors and to develop compounds that are efficacious both in the short and long term.

Therefore, it would be useful to provide methods and compositions for treatment of diabetes, chronic kidney failure, or high blood glucose levels.

SUMMARY OF THE DISCLOSURE

It has now surprisingly been discovered that alpha 7 (α7) nicotinic acetylcholine receptor modulators are useful to treat diabetes mellitus, chronic kidney disease consequent to diabetic neuropathy, acute kidney failure, nicotine-exacerbated chronic kidney disease, chronic kidney disease in the absence of nicotine exacerbation, and reduction of blood glucose levels.

It is contemplated by the present disclosure that the compounds and formulas disclosed herein could act as alpha 7 (α7) nicotinic acetylcholine receptor antagonists.

It is an object of the present disclosure that the nicotinic receptor antagonists disclosed herein are reversible antagonists. Therefore, this is believed to present an advantage over α-neurotoxins which are considered as essentially irreversible antagonists to the nAChR. Moreover, the compounds of the present disclosure are selective for α7 nAChR. For example, the compounds of the present disclosure bind very weakly or not at all to other nicotinic acetylcholine receptors including α4 β2 nAChR and neuromuscular receptors.

In one aspect of the present disclosure, the novel nicotinic receptors disclosed herein are less lipophilic and more polar than nicotinic acetylcholine receptor antagonists that have previously been disclosed or known in the prior art. Compared to other nicotinic acetylcholine receptor antagonists known in the art, and without being bound to any theory, the polar substitutions of the nicotinic acetylcholine receptor antagonists disclosed herein render these compounds less likely to cross the Blood Brain Barrier and, thus, less likely to have adverse central nervous system side effects.

It is further contemplated that the novel nicotinic receptor antagonists of the present disclosure will be active in the peripheral nervous system as potent nicotinic receptor antagonists. One benefit, of many, of the novel nicotinic receptor antagonists disclosed herein, is that said antagonists retain their potent activity in the peripheral nervous system while simultaneously lacking central nervous system toxicity.

For example, it is contemplated that the nicotinic receptor modulators, i.e., antagonists, of the present disclosure may be used in the treatment of diabetes mellitus (i.e., type 1 diabetes and/or type 2 diabetes). It is further contemplated that the nicotinic receptor modulators of the present disclosed herein may be used in the treatment of chronic kidney disease consequent to diabetic neuropathy, acute kidney failure, nicotine-exacerbated chronic kidney disease, chronic kidney disease in the absence of nicotine exacerbation, and reduction of blood glucose levels.

In still another aspect of the present disclosure the nicotinic receptor modulators disclosed herein could be used, either alone or combination with another pharmaceutical, to treat one or more symptoms of diabetes. It is contemplated by the present disclosure that the nicotinic receptor modulators disclosed herein may treat at least one symptom of diabetes wherein that symptom of diabetes relates to high blood sugar, polyuria, proteinuria, feelings of frequent thirstiness or hunger, fatigue, impaired vision, impaired wound healing, and/or weight loss.

It is contemplated by the present disclosure that the nicotinic receptor modulators disclosed herein may also treat chronic kidney disease (i.e., chronic kidney disease consequent to diabetic neuropathy and/or nicotine-exacerbated chronic kidney disease) or at least one symptom of chronic kidney disease.

It is contemplated by the present disclosure that the nicotinic receptor modulators disclosed herein may also treat acute kidney failure (i.e., acute kidney failure consequent to renal injury, acute kidney failure consequent to chemotherapy and/or nicotine-exacerbated acute kidney failure) or at least one symptom of acute kidney failure.

In another aspect of the present disclosure, it is further contemplated that the disclosed α7 nAChR selective modulators may be used as research or diagnostic tools. It is further contemplated that novel α7 nAChR selective modulators could be used as a research tool in elucidating signal transduction in neuronal tissue. It is also contemplated that novel α7 nAChR selective modulators could be used as a research tool in elucidating signal transduction pathway in non-neuronal tissue as well.

Compounds of the disclosure may exist in free or salt form, e.g. as acid addition salts. In the specification unless otherwise indicated language such as compounds or formulas or compounds of the disclosure are to be understood as embracing the compounds in any form, for example free or acid addition salt form, or where the compounds contain acid substituents, in base addition salt form. Or where compounds contain basic substituents, in acid addition salt form. The compounds disclosed herein are intended for use as pharmaceuticals, therefore pharmaceutically acceptable salts are preferred. Salts which are unsuitable for pharmaceutical uses may be useful, for example, for the isolation or purification of free compounds, formulas, or compounds of the disclosure or their pharmaceutically acceptable salts, are therefore also included.

DETAILED DESCRIPTION OF THE DISCLOSURE

The examples provided in the detailed description are merely examples, which should not be used to limit the scope of the claims in any claim construction or interpretation.

The present disclosure contemplates use of a nicotinic acetylcholine receptor modulators, i.e., antagonists, of Formula I (below) in methods for treatment of diabetes, nicotine-exacerbated chronic kidney disease, chronic kidney disease in the absence of nicotine exacerbation, and reduction of blood glucose levels, the nicotinic acetylcholine receptor modulators of Formula I:

Formula I

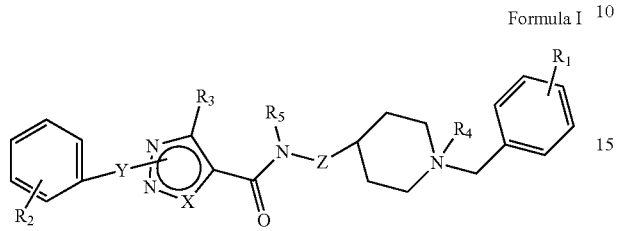

wherein $R_1$ and $R_2$ are independently halogen (e.g. Cl), $-SO_2NH_2$, or $-COOH$, e.g., in para-(4-) position, or H (i.e., phenyl is unsubstituted);
Y and Z are independently a bond or $-CH_2-$;
X is N or $CR_6$;
$R_3$, $R_5$ and $R_6$ are independently H, aryl, or lower (e.g. $C_{1-4}$) alkyl, e.g. methyl, ethyl or propyl;
$R_4$ is lower alkyl, e.g., methyl, or $R_4$ is not present;
in free or pharmaceutically acceptable salt form;
provided that when $R_4$ is lower alkyl, the compound forms a quaternary ammonium salt and there is an associated pharmaceutically acceptable anion present, e.g., halide, for example chloride, bromide or iodide.

For example, the disclosure provides compounds of Formula 1, as follows:

1.1. A compound of Formula I wherein $R_1$ is H or deuterium.
1.2. A compound of Formula I wherein $R_1$ is $-SO_2NH_2$.
1.3. A compound of Formula I wherein $R_1$ is $-COOH$.
1.4. A compound of any of the preceding scopes wherein $R_2$ is $-SO_2NH_2$.
1.5. A compound of Formula I or 1.1, 1.2, or 1.3 wherein $R_2$ is H or deuterium.
1.6. A compound of Formula I or 1.1, 1.2, or 1.3 wherein $R_2$ is $-COOH$.
1.7. A compound of any of the preceding scopes wherein X is N and Y is attached to the 2-nitrogen of the 1,2,3-triazole ring.
1.8. A compound of any of Formula I or 1.1-1.6 wherein X is N and Y is attached to the 1-nitrogen of the 1,2,3-triazole ring.
1.9. A compound of any of Formula I or 1.1-1.6 wherein X is C and Y is attached to the 2-nitrogen of the 1,2,3-triazole ring.
1.10. A compound of any of Formula I or 1.1-1.6 wherein X is C and Y is attached to the 1-nitrogen of the 1,2,3-triazole ring.
1.11. A compound of Formula I or any of the preceding scopes wherein $R_3$ is H.
1.12. A compound of Formula I or any of 1.1-1.10 wherein $R_3$ is aryl.
1.13. A compound of Formula I or any of 1.1-1.10, 1.12 wherein $R_3$ is phenyl or tolyl.
1.14. A compound of Formula I or any of 1.1-1.10, 1.12-1.13 wherein $R_3$ is phenyl.
1.15. A compound of Formula I or any of 1.1-1.10 or 1.12-1.13 wherein $R_3$ is tolyl.
1.16. A compound of Formula I or any of 1.1-1.1.10 wherein $R_3$ is lower (e.g. $C_{1-4}$) alkyl.
1.17. A compound of Formula I or any of 1.1-1.1.10, 1.16 wherein $R_3$ is methyl, ethyl, or propyl.
1.18. A compound of Formula I or any of the preceding scopes wherein $R_4$ is not present.
1.19. A compound of Formula I or any of 1.1-1.1.17 wherein $R_4$ is lower alkyl.
1.20. A compound of Formula I or any of 1.1-1.1.17 or 1.19 wherein $R_4$is methyl.
1.21. A compound of Formula I or any of the preceding scopes wherein $R_5$ is H.
1.22. A compound of Formula I or any of 1.1-1.20 wherein $R_5$ is aryl.
1.23. A compound of Formula I or any of 1.1-1.20 or 1.22 wherein $R_5$ is phenyl or tolyl.
1.24. A compound of Formula I or 1.1-1.20 or 1.22-1.23 wherein $R_5$ is phenyl.
1.25. A compound of Formula I or any of 1.1-1.20 wherein $R_5$ is tolyl.
1.26. A compound of Formula I or any of 1.1-1.20 wherein $R_5$ is lower (e.g. $C_{1-4}$) alkyl.
1.27. A compound of Formula I or any of 1.1-1.20 wherein $R_5$ is methyl, ethyl, or propyl.
1.28. A compound of Formula I or any of 1.1-20 or 1.27 wherein $R_5$ is methyl.
1.29. A compound of Formula I or any of 1.1-20 or 1.27 wherein $R_5$ is ethyl.
1.30. A compound of Formula I or any of 1.1-20 or 1.27 wherein $R_5$ is propyl.
1.31. A compound of Formula I or any of 1.1-1.30 wherein $R_6$ is H.
1.32. A compound of Formula I or any of 1.1-1.30 wherein $R_6$ is aryl.
1.33. A compound of Formula I or any of 1.1-1.30 or 1.32 wherein $R_6$ is phenyl or tolyl.
1.34. A compound of Formula I or any of 1.1-1.30 or 1.32-1.33 wherein $R_6$ is phenyl.
1.35. A compound of Formula I or any of 1.1-1.30 or 1.32-1.33 wherein $R_6$ is tolyl.
1.36. A compound of Formula I or any of 1.1-1.35 wherein $R_6$ is lower (e.g. $C_{1-4}$) alkyl.
1.37. A compound of Formula I or any of 1.1-1.36 wherein $R_6$ is methyl, ethyl, or propyl.
1.38. A compound of Formula I or any of 1.1-1.37 wherein $R_6$ is methyl.
1.39. A compound of Formula I or any of 1.1-1.37 wherein $R_6$ is ethyl.
1.40. A compound of Formula I or any of 1.1-1.37 wherein $R_6$ is propyl.
1.41. Any of the preceding scopes wherein Y is methylene.
1.42. Any of the preceding scopes wherein Z is methylene.

For example, Compounds of Formula I include diazole compounds, e.g., compound 1-6:

Compound 1
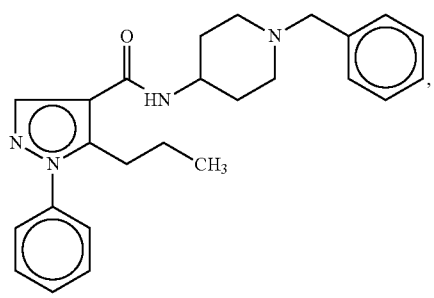
Compound 2
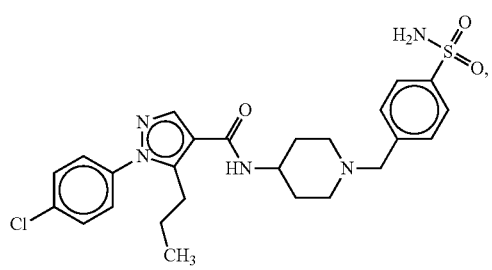
Compound 3
Compound 4
Compound 5
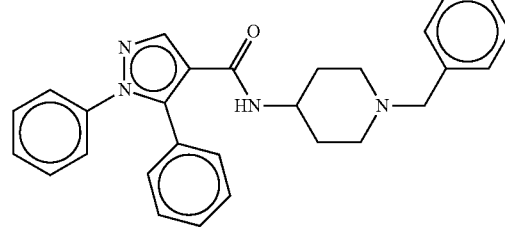
Compound 6
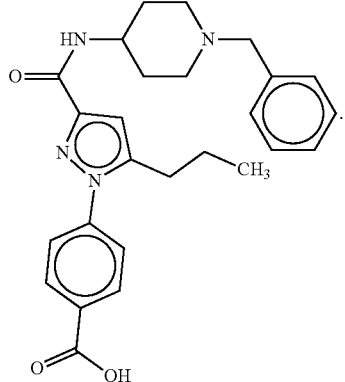
Compounds of Formula I also include triazole compounds, e.g., compounds 7-18:
Compound 7
Compound 8
Compound 9
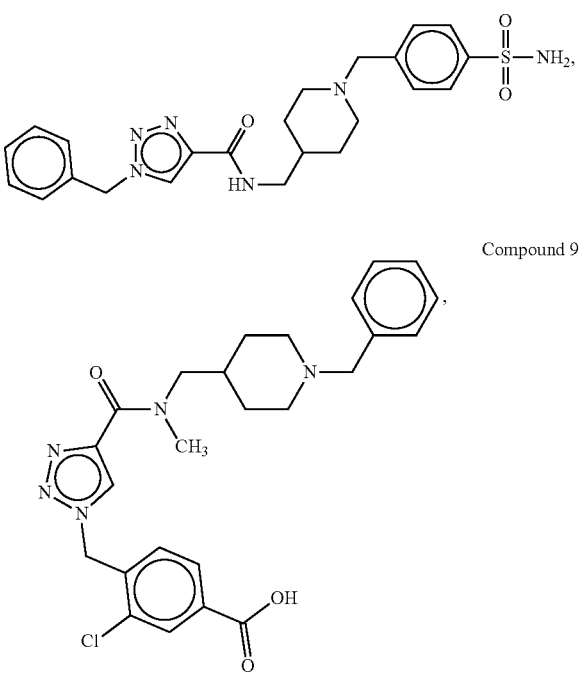
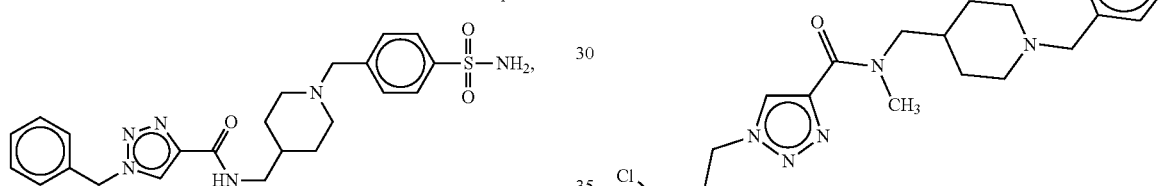
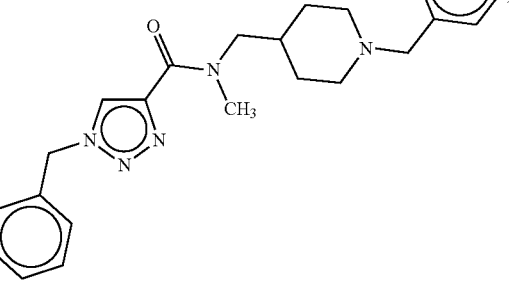

Compound 10
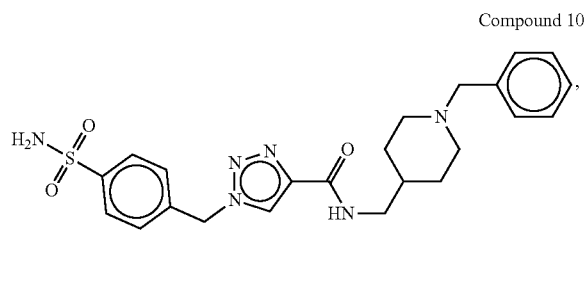
Compound 11
Compound 14
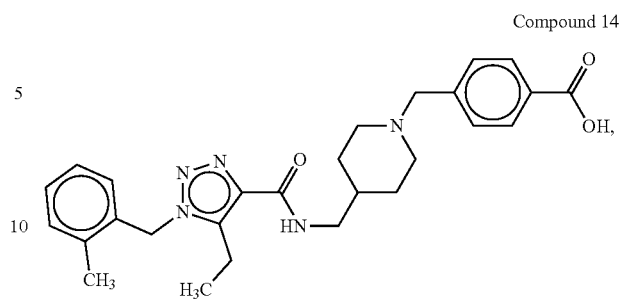
Compound 15
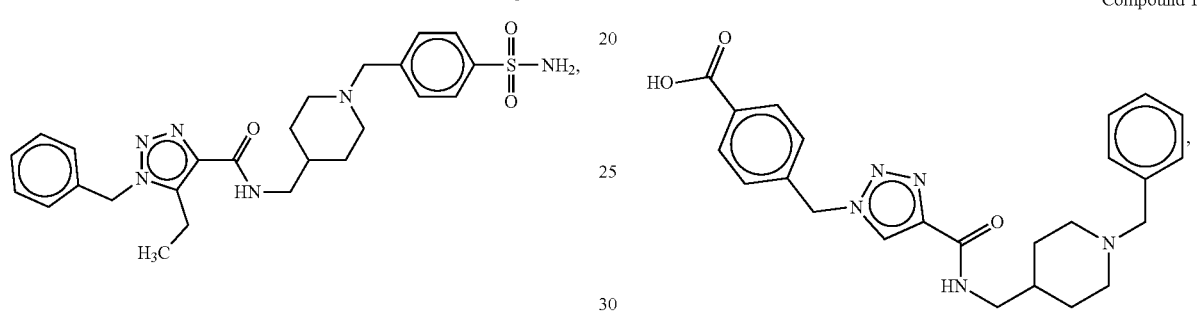
Compound 12
Compound 16
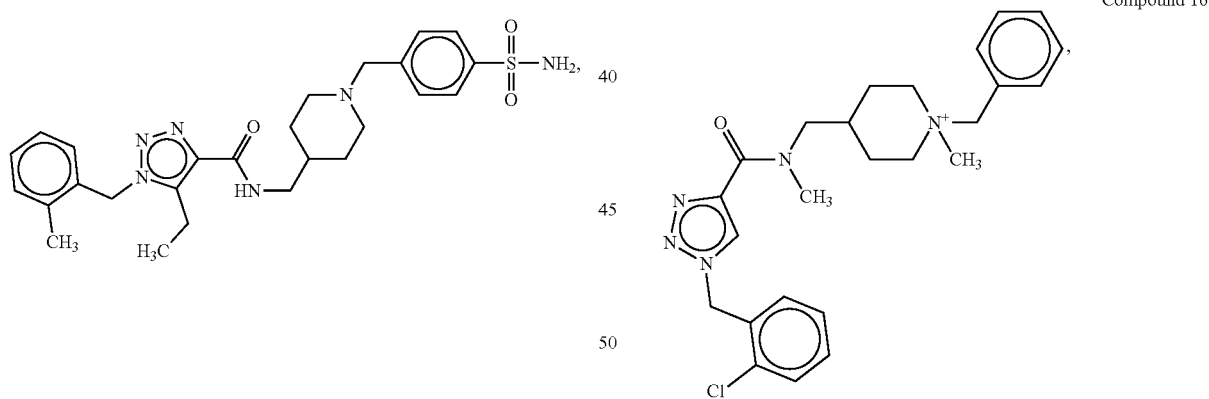
Compound 13
Compound 17, and
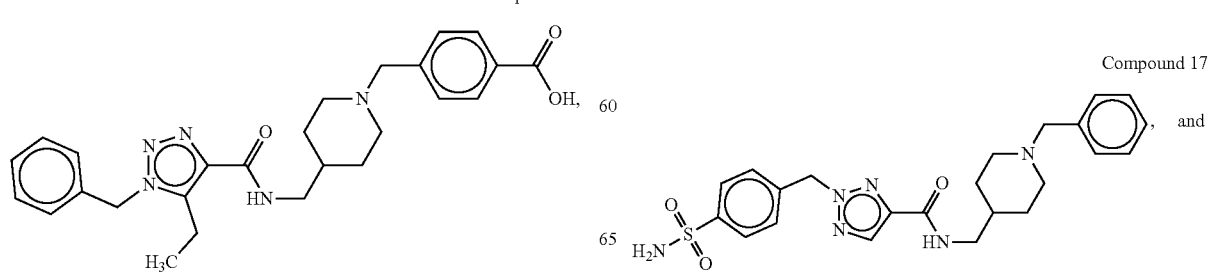

Compound 18

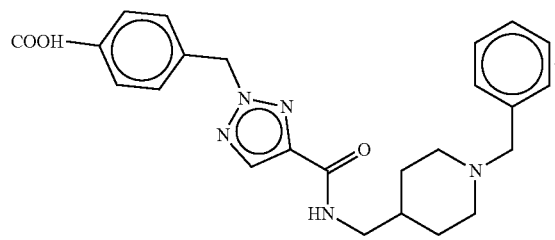

For example, Compounds of Formula I include compounds of Formula II:

Formula II

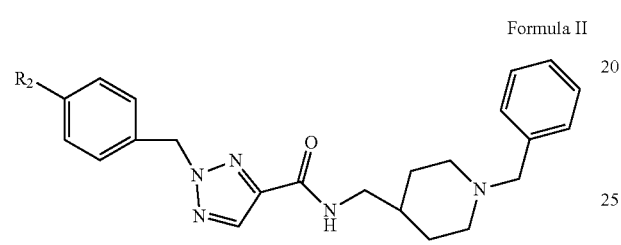

wherein $R_2$ is halogen (e.g. Cl or F), —SO$_2$NH$_2$, or —COOH, in free or pharmaceutically acceptable acid or base addition salt form, including quaternary ammonium salt form, e.g., methyl halide For example, the disclosure provides for compounds of Formula II as follows:

1.43 Formula II, wherein $R_2$ is halogen.

1.44 Formula II of 1.34, wherein $R_2$ is Cl.

1.45 Formula II or 1.34, wherein $R_2$ is F.

1.46 Formula II, wherein $R_2$ is —SO$_2$NH$_2$.

1.47 Formula II, wherein $R_2$ is —COOH.

Compounds of Formula I and II preferably bind to the nicotinic acetylcholine receptor with a high affinity, e.g., with a $K_D$ binding affinity of less than 10 nM, preferably less than 1 nM.

For example, compounds 1-18 have a $K_D$ binding affinity of 0.7 nM or less.

In one aspect of the present disclosure the general synthesis of compound of Formula I wherein R4 is lower alkyl is depicted in exemplary Scheme 1. Eleven mg of compound wherein $R_4$ is not present and 6 µL methyl iodide (CH$_3$I) are dissolved in 1.0 mL acetone at room temperature. Under stirring, 8.0 mg K$_2$CO$_3$ is added and the mixture is stirred overnight at room temperature. The white solid is filtrated and the solution is concentrated to leave the residue as colorless oil. In the example depicted, the residue is purified on HPLC to give 9.0 mg of the product as colorless oil and with purity >98% and yield about 79%.

Scheme 1.

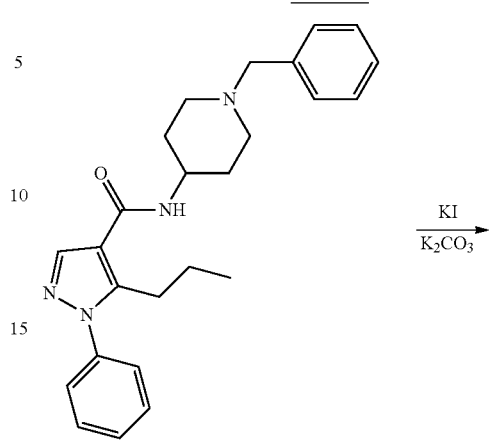

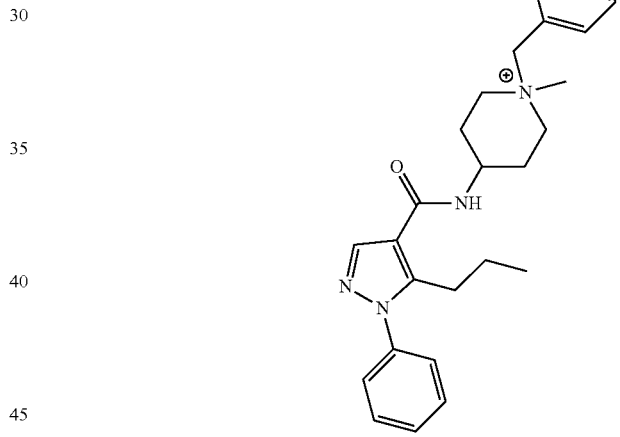

In another aspect of the present disclosure the general synthesis of a triazole compound of Formula I is depicted in Scheme 2. In this example, Compound 1 of the Scheme 2 is coupled with compound 2 of Scheme 2 at the presence of an activating agent BOP to give product 3 of Scheme 2, which then alkylated with substituted benzyl bromide 4 of Scheme 2 to produce the desired product 6 of Scheme 2 and by product 5 of Scheme 2. Compound 6 of Scheme 2 is purified by a silica gel column and then reacted with TFA to cleave the Boc group. Compound 7 of Scheme 2 is alkylated with benzyl bromide, and the reaction mixture is purified by HPLC to yield final product compound of Formula I, which in the exemplified scheme is a white solid with purity >98%, overall yield about 32%.

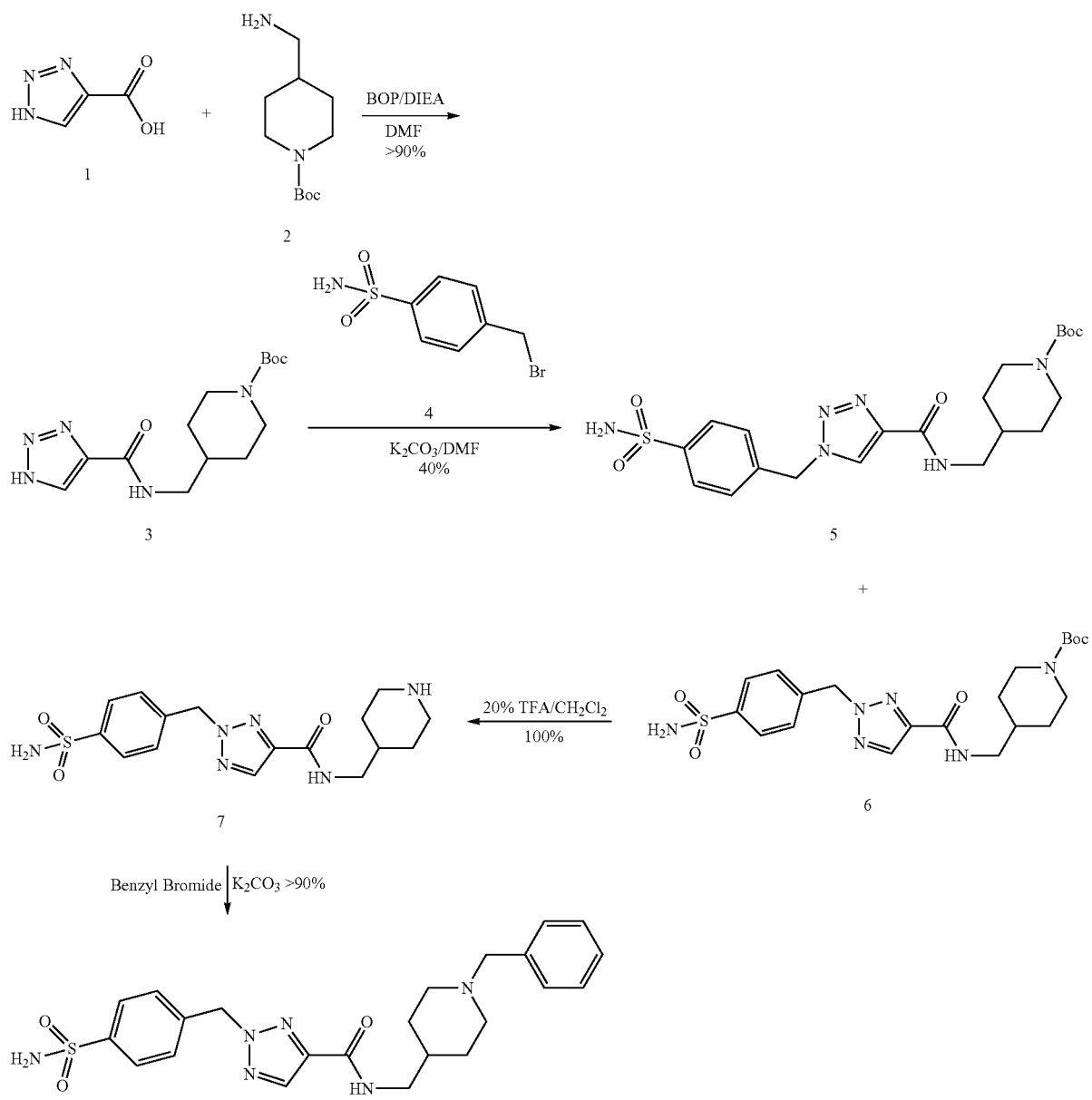

Other Compounds of Formulas I and II are made analogously.

The present disclosure also provides Method I for the treatment or prophylaxis of a disease or disorder characterized by the activation of an acetylcholine receptor pathway, comprising administering to the patient an effective amount of a α7 nicotinic acetylcholine receptor modulators, i.e., antagonists, according to Formula I or Formula II in a free or pharmaceutically acceptable salt form, for example:

1.1 Method I, wherein said disease or disorder is diabetes mellitus, chronic kidney disease consequent to diabetic neuropathy, acute kidney failure, nicotine-exacerbated chronic kidney disease, chronic kidney disease in the absence of nicotine exacerbation, and reduction of blood glucose levels.

1.2 Method I or Method 1.1, wherein said disease or disorder is diabetes mellitus.

1.3 Method I or Method 1.1, wherein said disease or disorder is chronic kidney disease.

1.4 Method I or any of Method 1.1 or 1.3, wherein said chronic kidney disease is exacerbated by nicotine.

1.5 Method I or any of Method 1.1 or 1.3, wherein said chronic kidney disease is not exacerbated by nicotine.

1.6 Method I or any of Method 1.1 or 1.3, wherein said chronic kidney disease consequent to diabetic neuropathy.

1.7 Method I or Method 1.1, wherein said disease or disorder is acute kidney failure (i.e. acute kidney failure consequent to renal injury, acute kidney failure consequent to chemotherapy or nicotine-exacerbated acute kidney failure).

1.8 Method I or any of Methods 1.1 or 1.2, wherein said disease or disorder is a symptom of diabetes mellitus, e.g., high blood pressure, high blood glucose, high proteinuria content (e.g., albuminuria), weight loss, impaired vision, polyuria, impaired wound healing, fatigue or nerve damage.

1.9 Method I or Method 1.8, wherein high blood glucose comprises a concentration sufficient to manifest deleterious effects of diabetes mellitus.

1.10 Method I or Method 1.8, wherein high blood glucose comprises a concentration of at least 180 mg/dL.

1.11 Method I or any of Methods 1.1-1.10, wherein the patient is a human.

1.12 Method I or any of Methods 1.1-1.11, wherein said disease or disorder is characterized by the presence of high blood pressure, high blood glucose, high proteinuria content (e.g., albuminuria), weight loss, impaired vision, polyuria, impaired wound healing, fatigue or nerve damage.

1.13 Method I or any of methods 1.1-1.12, wherein a patient is suffering from or at risk for developing diabetes mellitus.

1.14 Method I or any of methods 1.1-1.13, wherein a patient is administered an effective amount of a novel α7 nicotinic acetylcholine receptor modulator of Formula I or Formula II (e.g., any of Compounds 1.1-1.47) in a pharmaceutically acceptable carrier.

1.15 Method I or Method 1.14, wherein the α7 nicotinic acetylcholine receptor modulators according to Formula I or Formula II (e.g., any of Compounds 1.1-1.47) are used to treat at least one of the symptoms of diabetes mellitus, e.g. high blood pressure, high blood glucose, high proteinuria content (e.g., albuminuria), weight loss, impaired vision, polyuria, impaired wound healing, fatigue or nerve damage.

1.16 Method I or any of methods 1.1-1.15, wherein the patient is administered an effective amount of an α7 nicotinic acetylcholine receptor modulator according to Formula I (e.g., any of Compounds 1.1-1.42).

1.17 Method I or any of methods 1.1-1.16, wherein the patient is administered an effective amount of an α7 nicotinic acetylcholine receptor modulator according to Formula II (e.g., any of Compounds 1.43-1.47).

1.18 Method I or any of methods 1.1-1.17, wherein a patient is administered an effective amount of a novel α7 nicotinic acetylcholine receptor modulator of Formula I or Formula II (e.g., any of Compounds 1.1-1.47) in a pharmaceutically acceptable carrier.

1.19 Method I or any of methods 1.1-1.18, wherein a pharmaceutical composition comprising a compound according to Formula I or Formula II (e.g., any of Compounds 1.1-1.47) in admixture with a pharmaceutically acceptable diluent or carrier.

1.20 Method I or any of methods 1.1-1.19, wherein the patient is administered an effective amount of an α7 nicotinic acetylcholine receptor modulator according to Formula I, e.g., selected from compounds 1-18.

1.21 Method I or any of methods 1.1-1.20, wherein the patient is administered an effective amount of an α7 nicotinic acetylcholine receptor modulator which is compound 17.

1.22 Method I or any of methods 1.1-1.21, wherein the patient is administered an effective amount of an α7 nicotinic acetylcholine receptor modulator orally.

1.23 Method I or any of methods 1.1-1.22, wherein the patient is administered an effective amount of an α7 nicotinic acetylcholine receptor modulator parenterally.

1.24 Method I or any of methods 1.1-1.23, wherein the patient is administered an effective amount of an α7 nicotinic acetylcholine receptor modulator by injection, e.g., subcutaneously, intramuscularly, intravenously, or intrathecally, e.g., a bolus administered subcutaneously, intramuscularly, intravenously, or intrathecally.

1.25 Method I or any of methods 1.1-1.24, wherein the patient is administered an effective amount of an α7 nicotinic acetylcholine receptor modulator intravenously, e.g., IV bolus and/or IV infusion, e.g., IV bolus followed by IV infusion.

In a further embodiment, provided is a method (Method A) of inhibiting α7 nicotinic acetylcholine receptor function in vivo comprising administering a compound according to Formula I or Formula II, e.g., compound 1.1 to 1.47.

Further provided is Method A as follows:

A.1 Method A, wherein the compound is administered orally.

A.2 Method A, wherein the pharmaceutical composition is administered parenterally.

A.3 Method of A.2, wherein the pharmaceutical composition is administered intravenously, e.g., IV bolus and/or IV infusion, e.g., IV bolus followed by IV infusion.

The present disclosure also provides Method B for the treatment or prophylaxis of chronic kidney disease consequent to diabetic neuropathy, acute kidney failure, nicotine-exacerbated chronic kidney disease, or chronic kidney disease in the absence of nicotine exacerbation, comprising administering to the patient an effective amount of a α7 nicotinic acetylcholine receptor modulator, i.e., antagonist, according to Formula I or Formula II in a free or pharmaceutically acceptable salt form, for example:

B.1 Method B, wherein said disease or disorder is chronic kidney disease.

B.2 Method B or B.1, wherein said chronic kidney disease is exacerbated by nicotine.

B.3 Method I or any of Method 1.1 or 1.3, wherein said chronic kidney disease is not exacerbated by nicotine.

B.4 Method B or B.1, wherein said chronic kidney disease consequent to diabetic neuropathy.

B.5 Method B, wherein said disease or disorder is acute kidney failure (i.e. acute kidney failure consequent to renal injury, acute kidney failure consequent to chemotherapy or nicotine-exacerbated acute kidney failure).

B.6 Method B or any of Methods B.1-B.5, wherein the patient is a human.

B.7 Method B or any of Methods B.1-B.6, wherein said disease or disorder is characterized by the presence of high blood pressure, high blood glucose, high proteinuria content (e.g., albuminuria), weight loss, impaired vision, polyuria, impaired wound healing, fatigue or nerve damage.

B.8 Method B or any of methods B.1-B.7, wherein a patient is administered an effective amount of a novel α7 nicotinic acetylcholine receptor modulator of Formula I or Formula II (e.g., any of Compounds 1.1-1.47) in a pharmaceutically acceptable carrier.

B.9 Method B or any of methods B.1-B.8, wherein the patient is administered an effective amount of an α7 nicotinic acetylcholine receptor modulator according to Formula I (e.g., any of Compounds 1.1-1.42).

B.10 Method B or any of methods B.1-B.8, wherein the patient is administered an effective amount of an α7 nicotinic acetylcholine receptor modulator according to Formula II (e.g., any of Compounds 1.43-1.47).

B.11 Method B or any of methods B.1-B.10, wherein a patient is administered an effective amount of a novel α7 nicotinic acetylcholine receptor modulator of Formula I or Formula II (e.g., any of Compounds 1.1-1.47) in a pharmaceutically acceptable carrier.

B.12 Method B or any of methods B.1-B.11, wherein a pharmaceutical composition comprising a compound according to Formula I or Formula II (e.g., any of Compounds 1.1-1.47) in admixture with a pharmaceutically acceptable diluent or carrier.

B.13 Method B or any of methods B.1-B.12, wherein the patient is administered an effective amount of an α7 nicotinic acetylcholine receptor modulator according to Formula I, e.g., selected from compounds 1-18.

B.14 Method B or any of methods B.1-B.13, wherein the patient is administered an effective amount of an α7 nicotinic acetylcholine receptor modulator which is compound 17.

B.15 Method B or any of methods B.1-B.14, wherein the patient is administered an effective amount of an α7 nicotinic acetylcholine receptor modulator orally.

B.16 Method B or any of methods B.1-B.14, wherein the patient is administered an effective amount of an α7 nicotinic acetylcholine receptor modulator parenterally.

B.17 Method B or any of methods B.1-B.14, wherein the patient is administered an effective amount of an α7 nicotinic acetylcholine receptor modulator by injection, e.g., subcutaneously, intramuscularly, intravenously, or intrathecally, e.g., a bolus administered subcutaneously, intramuscularly, intravenously, or intrathecally.

B.18 Method B or any of methods B.1-B.14, wherein the patient is administered an effective amount of an α7 nicotinic acetylcholine receptor modulator intravenously, e.g., IV bolus and/or IV infusion, e.g., IV bolus followed by IV infusion.

The present disclosure also provides Method C for the treatment or prophylaxis of diabetes mellitus or reduction of blood glucose levels, comprising administering to the patient an effective amount of a α7 nicotinic acetylcholine receptor modulators, i.e., antagonists, according to Formula I or Formula II in a free or pharmaceutically acceptable salt form, for example:

C.1 Method C, wherein said disease or disorder is diabetes mellitus.

C.2 Method C or C.1, wherein said disease or disorder is a symptom of diabetes mellitus, e.g., high blood pressure, high blood glucose, high proteinuria content (e.g., albuminuria), weight loss, impaired vision, polyuria, impaired wound healing, fatigue or nerve damage.

C.3 Method C or Method C.1-C.2, wherein high blood glucose comprises a concentration sufficient to manifest deleterious effects of diabetes mellitus.

C.4 Method C or Method C.3, wherein high blood glucose comprises a concentration of at least 180 mg/dL.

C.5 Method C or any of Methods C.1-C.4, wherein said disease or disorder is characterized by the presence of high blood pressure, high blood glucose, high proteinuria content (e.g., albuminuria), weight loss, impaired vision, polyuria, impaired wound healing, fatigue or nerve damage.

C.6 Method C or any of Methods C.1-C.5, wherein a patient is suffering from or at risk for developing diabetes mellitus.

C.7 Method C or any of methods B.1-B.6, wherein a patient is administered an effective amount of a novel α7 nicotinic acetylcholine receptor modulator of Formula I or Formula II (e.g., any of Compounds 1.1-1.47) in a pharmaceutically acceptable carrier.

C.8 Method C or Method C.7, wherein the α7 nicotinic acetylcholine receptor modulator according to Formula I or Formula II (e.g., any of Compounds 1.1-1.47) are used to treat at least one of the symptoms of diabetes mellitus, e.g. high blood pressure, high blood glucose, high proteinuria content (e.g., albuminuria), weight loss, impaired vision, polyuria, impaired wound healing, fatigue or nerve damage.

C.9 Method C or any of methods C.1-C.8, wherein a pharmaceutical composition comprising a compound according to Formula I or Formula II (e.g., any of Compounds 1.1-1.47) in admixture with a pharmaceutically acceptable diluent or carrier.

C.10 Method C or any of methods C.1-C.9, wherein the patient is administered an effective amount of an α7 nicotinic acetylcholine receptor modulator according to Formula I, e.g., selected from compounds 1-18.

C.11 Method C or any of methods C.1-C.10, wherein the patient is administered an effective amount of an α7 nicotinic acetylcholine receptor modulator which is compound 17.

C.12 Method C or any of methods C.1-C.11, wherein the patient is administered an effective amount of an α7 nicotinic acetylcholine receptor modulator orally.

C.13 Method C or any of methods C.1-C.12, wherein the patient is administered an effective amount of an α7 nicotinic acetylcholine receptor modulator parenterally.

C.14 Method C or any of methods C.1-C.13, wherein the patient is administered an effective amount of an α7 nicotinic acetylcholine receptor modulator by injection, e.g., subcutaneously, intramuscularly, intravenously, or intrathecally, e.g., a bolus administered subcutaneously, intramuscularly, intravenously, or intrathecally.

C.15 Method C or any of methods C.1-C.14, wherein the patient is administered an effective amount of an α7 nicotinic acetylcholine receptor modulator intravenously, e.g., IV bolus and/or IV infusion, e.g., IV bolus followed by IV infusion.

In yet another embodiment, provided is a pharmaceutical composition comprising a compound according to Formula I or Formula II, e.g., compound 1.1 to 1.47, for use in treatment or prophylaxis of a disease or disorder characterized by the activation of an acetylcholine receptor pathway.

In yet another embodiment, provided is a pharmaceutical composition comprising a compound according to Formula I or Formula II, e.g., compound 1.1 to 1.47, for use in any of Methods 1, e.g., 1.1-1.25; any of Methods A, e.g., A.1-A.3; any of Methods B, e.g., B.1-B.18; or any of Methods C, e.g., C.1-C.15.

In a particular embodiment, provided is a pharmaceutical composition comprising a compound according to Formula I or Formula II, e.g., compound 1.1 to 1.47, for use in any of Methods 1, e.g., 1.1-1.25; any of Methods A, e.g., A.1-A.3; any of Methods B, e.g., B.1-B.18; or any of Methods C, e.g., C.1-C.15, that is administered in an immediate release or sustained or delayed release formulation, e.g., depot formulation.

In one embodiment, the sustained or delayed release formulation comprises the Compounds of Formula I disclosed herein (e.g., the compound of Formula I or Formula II, e.g., compound 1.1 to 1.47) in a polymeric matrix. In another embodiment, the Compounds of Formula I or Formula II are dispersed or dissolved within the polymeric matrix. In a further embodiment, the polymeric matrix comprises standard polymers used in depot formulations such as polymers selected from a polyester of a hydroxy fatty acid and derivatives thereof, or a polymer of an alkyl alpha-cyanoacrylate, a polyalkylene oxalate, a poly(ortho) ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 75:25, PLGA 85:15 and PLGA 90:10 polymer. In another embodiment, the polymer is selected from poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a particular embodiment, the polymeric matrix comprises poly (d,l-lactide-co-glycolide). The Compound of Formula I or Formula II in a polymeric matrix may be in admixture or in association with a pharmaceutically acceptable diluent or carrier.

The sustained or delayed release formulations as hereinbefore described are particularly useful for sustained or delayed release, wherein the Compounds of Formula I or Formula II are released upon degradation of the polymeric matrix. These formulations may release the Compounds of Formula I or Formula II over a period of up to 180 days, e.g., from about 14 to about 30 to about 180 days. For example, the polymeric matrix may degrade and release the Compounds of Formula I or Formula II over a period of about 30, about 60 or about 90 days. In another example, the polymeric matrix may degrade and release the Compounds of Formula I or Formula II over a period of about 120, or about 180 days.

The selectivity of these compounds is measured on the neuronal α4β2 and the muscle-type nAChRs using methods known in the art. At 10 μM, all tested compounds showed selectivity for the α7 nAChR over other two nicotinic receptors. Compound 16, for example, exhibits 92% binding to the α7 receptor and no detectable binding to the neuronal α4β2 and muscle-type nAChRs.

The pharmacokinetic (PK) study of compounds are performed in male C57Bl/6 mice (n=3 per time point) after an oral administration at 10 mg/kg to evaluate the brain penetrability. The concentrations of representative Compound 16 in brain and plasma are 0.15 μM and 0.2 μM at time t=2 h, respectively. The $t_{max}$ of Compound Q is probably longer than 2 h.

Three-dimensional structural models of human α7 nAChR are developed using homology modeling based on a known antagonist bound A-AChBP crystal structures. Docking studies are conducted to predict the binding poses of these novel nicotinic antagonists.

In accordance with this detailed description, the following abbreviations and definitions apply. It must be noted that as used herein, the singular forms "a", "and", and "the" include plural referents unless the context clearly dictates otherwise. Thus, for example, reference to "a compound" includes a plurality of such compounds and reference to "the dosage" includes reference to one or more dosages and equivalents thereof known to those skilled in the art, and so forth.

The terms "treating," "treatment," and the like are used herein to generally mean obtaining a desired pharmacological and physiological effect. The novel α7 nAChRs described herein which are used to treat a subject generally are provided in a therapeutically effective amount to achieve any one or more of the following: treatment of diabetes mellitus (e.g., reducing blood glucose levels, proteinuria, and/or polyuria), treatment of chronic kidney disease, or treatment of acute kidney failure. The term "treatment", as used herein, covers any treatment of a disease in any mammal, particularly a human, known to those that are skilled in the art.

The term "subject" or "patient" as used herein is meant to include a mammal. In a preferred aspect of the present disclosure the mammal is a human. In another preferred aspect of the present disclosure the mammal is a domestic animal.

The term "pharmaceutically effective" as used herein refers to the effectiveness of a particular treatment regime. Pharmaceutical efficacy can be measured based on such characteristics, for example, as: reducing blood glucose levels, insulin levels proteinuria, and/or polyuria. Diabetes is known to be associated with various cardiovascular conditions including, for example, accelerated atherosclerosis, endothelial dysfunction, cardiac fibrosis, myocardial inflammation, vascular calcification, biomechanical myocardial stress, oxidative stress, and cardiac myocyte injury. These conditions exhibit various biomarkers that recent studies suggest are associated with diabetes. Biomarkers associated with cardiac biomechanical stress and injury in relation to diabetes include, for example, elevated levels of natriuretic peptide (e.g., NT-proBNP), cardiac troponins (e.g. hs-cTnT), and copeptin. Biomarkers associated with myocardial inflammation in diabetic patients include, for example, elevated levels of C-reactive protein (CRP) (e.g., highly sensitive CRP), Galectin-3 (Gal-3), and matricellular proteins (e.g., osteoprotegerin and osteopontin). Growth differentiating factor-15 and fibroblast growth factor-23 have also been shown to be useful biomarkers in diabetic populations, as both exhibit elevated levels in diabetics when compared to healthy populations. Thus, a reduction of one or more of these biomarkers may be used to demonstrate pharmaceutical efficacy.

By "pharmaceutically effective amount" as used herein refers to the amount of an agent, reagent, compound, composition, or combination of reagents disclosed herein that when administered to a mammal that are determined to be sufficiently effective in the treatment of diabetes mellitus, chronic kidney disease consequent to diabetic neuropathy, acute kidney failure consequent to diabetic neuropathy, nicotine-exacerbated chronic kidney disease, chronic kidney disease in the absence of nicotine exacerbation, and reduction of blood glucose levels. A pharmaceutically effective amount will be known to those skilled in the art.

The term "nicotinic acetylcholine receptor" refers to the endogenous acetylcholine receptor having binding sites for acetylcholine which also bind to nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance that interacts with a receptor and increases or prolongs a physiological response (i.e. activates the receptor).

The term "partial agonist" refers to a substance that interacts with and activates a receptor to a lesser degree than an agonist.

The term "antagonist" refers to a substance that interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

EXAMPLES

The synthetic methods for various compounds of the present disclosure are illustrated below. Other compounds of the disclosure and their salts may be made using the methods as similarly described below and/or by methods similar to those generally described in the detailed description and by methods known in the chemical art.

Example 1—Role of the α7-nAchR on Nephropathy in Mouse Model of Diabetes

Normal mice express the α7-nAChR in both the proximal and distal tubule of the kidneys. Tests were conducted to determine the role of the α7-nAchR on the severity of nephropathy in a mouse model of diabetes. Diabetes mellitus (DM) was induced in all mice with streptozotocin (STZ). This test closely mimics diabetic neuropathy in humans. Mice were either given nicotine (DN) in doses of 100 m/ml in drinking water or tap water with no nicotine for a period of 10 weeks (DT). Targeted disruption of the endothelial nitric oxide synthase gene led to eNOS$^{-/-}$ knockout in a group of mice to increase susceptibility of STZ in the mice. One group of eNOS$^{-/-}$ knockout mice was also subjected to targeted disruption of the α7-nAchR gene, which led to eNOS$^{-/-}$/α7-nAchR$^{-/-}$ double knockout mice (DN$^{-/-}$ and DT$^{-/-}$). A separate group of eNOS$^{-/-}$ mice also received a α7-nAchR blocker (DN+B and DT+B). The blocker used was Compound 17 at a dosage of 2 mg/kg given intraperitoneally for 5 days a week for a period of 10 weeks. Blood pressure was measured by tail-cuff method and urine was collected every 2 weeks for albuminuria.

All mice became diabetic after being administered STZ, and all mice were also hypertensive. Results are summarized below in Table 1.

TABLE 1

|  | DN | DT | DN$^{-/-}$ | DT$^{-/-}$ | DN + B | DT + B |
|---|---|---|---|---|---|---|
| Body Weight (g) | 26 ± 1.0 | 22 ± 0.9 | 25 ± 1.9 | 23 ± 0.5 | 25 ± 0.5 | 26 ± 1.1 |
| Blood Glucose* (mg/dL) | 442 ± 48 | 542 ± 17 | 479 ± 41 | 516 ± 26 | 441 ± 43 | 354 ± 51 |
| Albuminuria ng/ml/24 hr* | 103 ± 25 | 71 ± 8 | 42 ± 14 | 46 ± 7 | 35 ± 6 | 50 ± 13 |
| Systolic BP (mmHg) | 153 ± 6 | 147 ± 6 | 153 ± 5 | 147 ± 4 | 142 ± 13 | 150 ± 11 |

*p < 0.05

All mice became diabetic after STZ and had no significant differences in weight or blood glucose at sacrifice (table). All animals were also hypertensive and nicotine had no effect on blood pressure in any of the groups. Diabetic mice receiving nicotine (DN) exhibited higher albumin excretion in comparison with diabetic mice on tap water (DT). Diabetic double knockout mice lacking the α7-nAchR (DN-/- and DT-/-) and α7-nAchR blocked mice (DN+B and DT+B) all showed significantly lower urinary excretions of albumin than diabetic mice on nicotine (DN). Surprisingly, diabetic mice on nicotine lacking the α7-nAchR or with pharmacologic blockade also exhibited urinary excretions of albumin that were lower than diabetics on tap water (DT). There was a trend towards lowering of protein urea in both the α7-nAchR knockout mice and with diabetic nice on tap water treated with the receptor blocker. This trend may indicate usefulness of the blocker in diabetic patients who do not smoke, which is a sizable and significant population.

These studies demonstrate that the α7-nAchR is a critical mediator of the deleterious effects of nicotine in the severity of diabetic nephropathy.

The invention claimed is:

1. A method of treatment of a disease or disorder characterized by the activation of an acetylcholine receptor pathway, comprising administering to a patient in need thereof an effective amount of a compound according to Formula I:

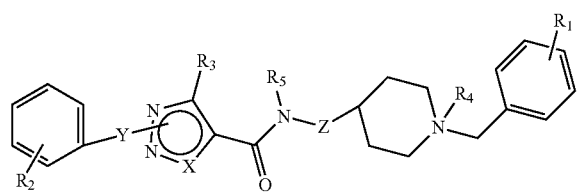

wherein $R_1$ and $R_2$ are independently halogen, —SO$_2$NH$_2$, or —COOH, or H;
Y and Z are independently a bond or —CH$_2$-;
X is N or CR$_6$;
$R_3$, $R_5$ and $R_6$ are independently H, phenyl, tolyl, or lower alkyl;
$R_4$ is lower alkyl, or $R_4$ is not present;
in free or pharmaceutically acceptable salt form;
provided that when $R_4$ is lower alkyl, the compound forms a quaternary ammonium salt and there is an associated pharmaceutically acceptable anion present;
wherein said disease or disorder is chronic kidney disease consequent to diabetic neuropathy, acute kidney failure, nicotine-exacerbated chronic kidney disease, or chronic kidney disease in the absence of nicotine exacerbation; wherein said disease or disorder is characterized by albuminuria; wherein administration of the effective amount of the compound according to Formula I to the patient reduces urinary excretion of albumin; and wherein the patient is a human.

2. A method of claim 1, wherein the compound is selected from one of compounds 1-18:

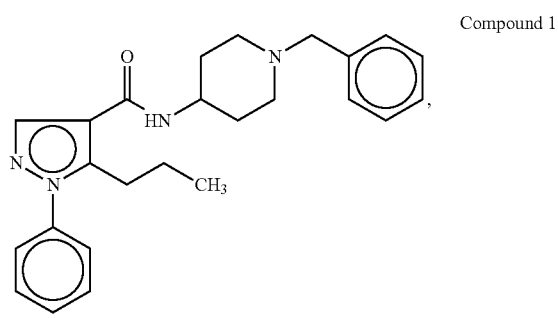

Compound 1

Compound 2
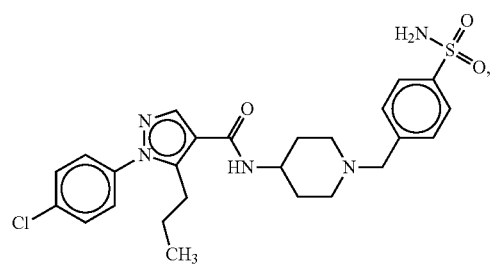
Compound 3
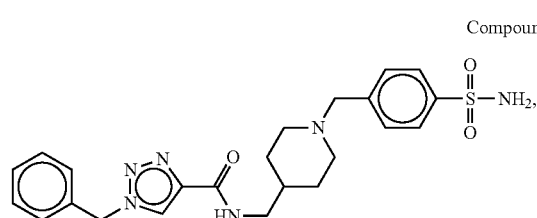
Compound 4
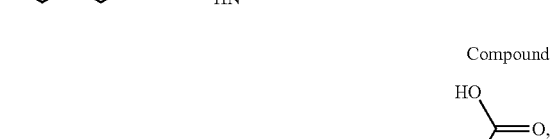
Compound 5
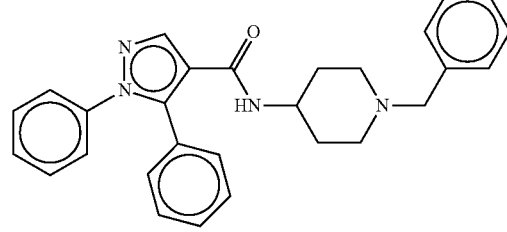
Compound 6
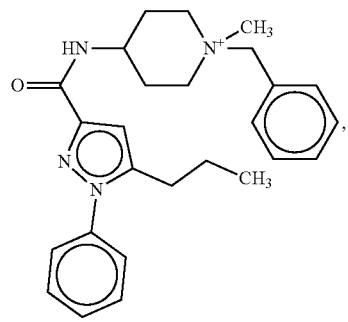
Compound 7
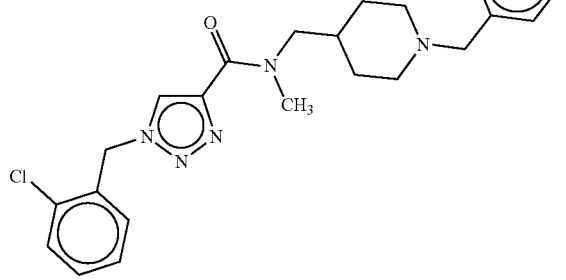
Compound 8
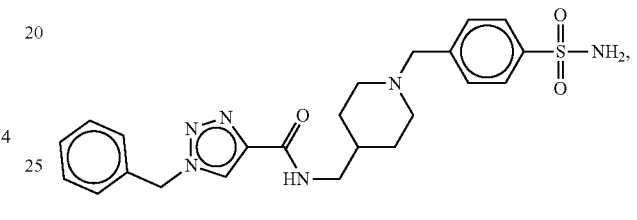
Compound 9, Compound 10, Compound 11
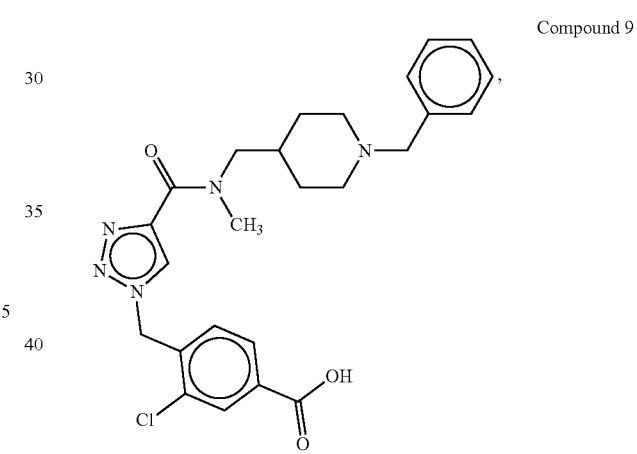

Compound 12
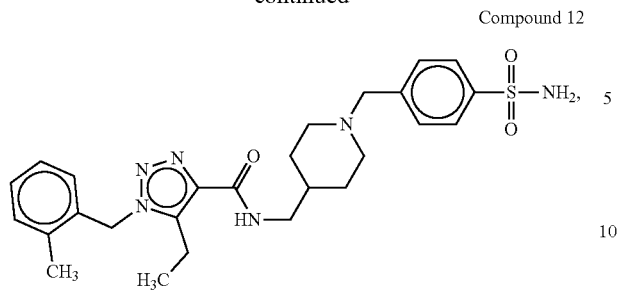

Compound 13
Compound 14
Compound 15
Compound 16
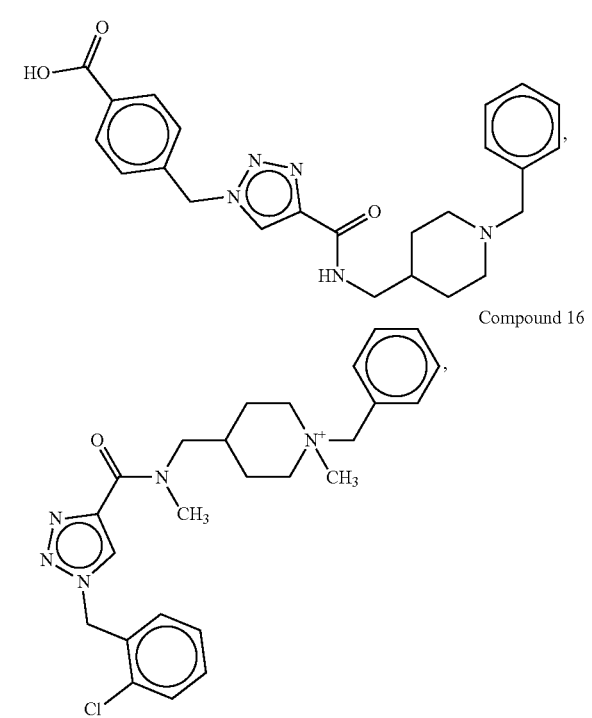

Compound 17
Compound 18
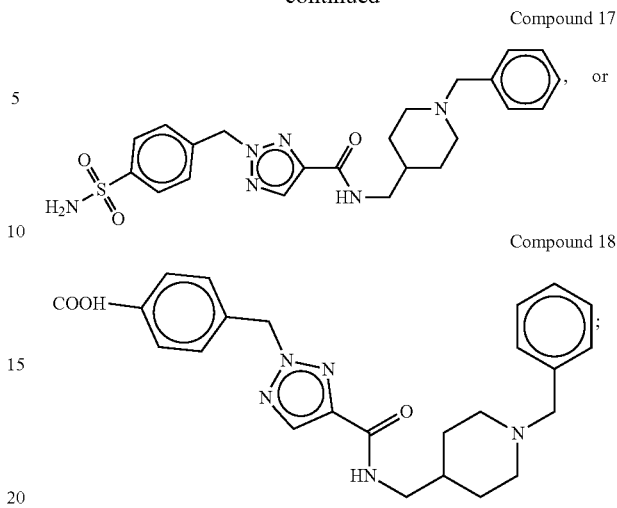

in free or pharmaceutically acceptable salt form.

3. A method of claim 1, wherein the compound is a compound of Formula II:

Formula II
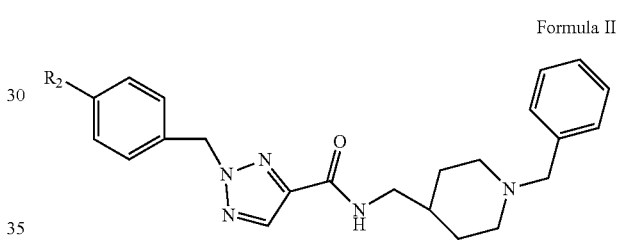

wherein $R_2$ is halogen, —$SO_2NH_2$, or —COOH, in free or pharmaceutically acceptable acid or base addition salt form, including quaternary ammonium salt form.

4. A method of claim 1, wherein said disease or disorder is chronic kidney disease consequent to diabetic neuropathy, nicotine-exacerbated chronic kidney disease, or chronic kidney disease in the absence of nicotine exacerbation.

5. A method of claim 1, wherein said disease or disorder is chronic kidney disease consequent to diabetic neuropathy.

6. A method of claim 1, wherein said disease or disorder is nicotine-exacerbated chronic kidney disease.

7. A method of claim 1, wherein said disease or disorder is acute kidney failure.

8. A method of claim 1, wherein said disease or disorder is characterized by the presence of high proteinuria content, weight loss, impaired vision, polyuria, impaired wound healing, fatigue or nerve damage.

9. A method of claim 1, wherein the compound according to Formula I is used to treat at least one of the symptoms of high proteinuria, weight loss, impaired vision, polyuria, impaired wound healing, fatigue or nerve damage.

10. A method of claim 1, wherein the patient is administered an effective amount of a pharmaceutical composition comprising the compound according to Formula I in admixture with a pharmaceutically acceptable diluent or carrier.

11. A method of claim 2, wherein the compound according to Formula I is compound 17.

12. A method of claim 7, wherein said acute kidney failure is acute kidney failure consequent to renal injury, acute kidney failure consequent to chemotherapy or nicotine-exacerbated acute kidney failure.

13. A method of claim 3, wherein the patient is administered an effective amount of a pharmaceutical composition comprising the compound according to Formula II in admixture with a pharmaceutically acceptable diluent or carrier.

14. A method of claim 11, wherein the patient is administered an effective amount of a pharmaceutical composition comprising compound 17 in admixture with a pharmaceutically acceptable diluent or carrier.

* * * * *